United States Patent
Smith

(10) Patent No.: US 9,131,675 B2
(45) Date of Patent: Sep. 15, 2015

(54) METHOD AND A KIT OF PARTS FOR DECONTAMINATING A MATTRESS OR OTHER EFFECTS

(75) Inventor: Colin Smith, West Sussex (GB)

(73) Assignee: MidMos Solutions Limited (GB)

( * ) Notice: Subject to any disclaimer, the term of this patent is extended or adjusted under 35 U.S.C. 154(b) by 758 days.

(21) Appl. No.: 13/265,119

(22) PCT Filed: Apr. 20, 2010

(86) PCT No.: PCT/GB2010/050644
§ 371 (c)(1),
(2), (4) Date: Jan. 4, 2012

(87) PCT Pub. No.: WO2010/122334
PCT Pub. Date: Oct. 28, 2010

(65) Prior Publication Data
US 2012/0096761 A1  Apr. 26, 2012

(30) Foreign Application Priority Data
Apr. 20, 2009 (GB) .................................. 0906754.7

(51) Int. Cl.
*A01M 1/20* (2006.01)
*A01M 17/00* (2006.01)
*A61L 2/235* (2006.01)
*A61L 2/238* (2006.01)
(Continued)

(52) U.S. Cl.
CPC .............. *A01M 17/006* (2013.01); *A01M 1/20* (2013.01); *A01M 1/2094* (2013.01); *A61L 2/235* (2013.01); *A61L 2/238* (2013.01); *A61L 2202/122* (2013.01); *A61L 2202/26* (2013.01); *B65D 81/268* (2013.01); *B65D 85/16* (2013.01)

(58) Field of Classification Search
CPC ..... A01M 1/20; A01M 13/00; A01M 13/003; A01M 1/2094
USPC .................................. 43/123–125, 132.1, 129
See application file for complete search history.

(56) References Cited

U.S. PATENT DOCUMENTS 3,625,888 A * 12/1971 Redmore et al. ................. 422/14
4,199,548 A * 4/1980 Kaiho et al. ..................... 43/125
(Continued)

FOREIGN PATENT DOCUMENTS

DE    4441797 A1 * 5/1996 ............ A01M 13/00
DE   19501783 A1 * 7/1996 ............ A01M 13/00
(Continued)

OTHER PUBLICATIONS

International Search Report for PCT/GB2010/050644.
(Continued)

*Primary Examiner* — Darren W Ark
(74) *Attorney, Agent, or Firm* — Fishman Stewart Yamaguchi PLLC

(57) ABSTRACT

The invention relates to a method for decontaminating a mattress (14) or other effect of bed bugs comprising the steps of: Placing the mattress or other effect in a hermetically sealable container (10) of a size and shape commensurate with that of the mattress or other effect; Inserting an appropriate quantity of an oxygen scavenger (16) into the container; Hermetically sealing the container so as to prevent ingress of oxygen; and Leaving it for a time sufficient for the oxygen levels to be depleted to less than 0.2% and the bed bugs and their eggs and larvae to be destroyed. It also relates to a kit of parts for implementing the method.

18 Claims, 3 Drawing Sheets

(51) Int. Cl.
*B65D 81/26* (2006.01)
*B65D 85/16* (2006.01)

(56) References Cited

U.S. PATENT DOCUMENTS

| | | | |
|---|---|---|---|
| 4,649,895 A * | 3/1987 | Yasuki et al. | 126/263.05 |
| 5,119,586 A * | 6/1992 | Townsend | 43/131 |
| 5,260,023 A * | 11/1993 | Evans, II | 422/40 |
| 5,282,322 A * | 2/1994 | Kasuya | 34/93 |
| 5,365,692 A * | 11/1994 | Gustafson | 43/132.1 |
| 5,378,428 A * | 1/1995 | Inoue et al. | 422/9 |
| 5,378,430 A * | 1/1995 | Nieves et al. | 422/426 |
| 6,399,387 B1 * | 6/2002 | Stenholm et al. | 422/420 |
| 6,835,571 B2 * | 12/2004 | Conlon et al. | 422/547 |
| 7,591,099 B2 * | 9/2009 | Lang et al. | 43/107 |
| 7,631,760 B2 * | 12/2009 | Guelzow et al. | 206/438 |
| 7,739,829 B2 * | 6/2010 | Chen et al. | 43/132.1 |
| 7,762,044 B2 * | 7/2010 | Clarke et al. | 422/22 |
| 7,765,733 B1 * | 8/2010 | Liu | 43/132.1 |
| 8,146,290 B1 * | 4/2012 | Telly | 43/123 |
| 8,278,628 B2 * | 10/2012 | Hamilton | 422/186.07 |
| 8,528,469 B2 * | 9/2013 | Doglioni Majer | 99/467 |
| 8,551,510 B2 * | 10/2013 | Bedoukian | 424/405 |
| 8,689,481 B2 * | 4/2014 | Lindsey | 43/132.1 |
| 8,707,616 B1 * | 4/2014 | Black et al. | 43/123 |
| 8,726,539 B2 * | 5/2014 | Potter et al. | 43/132.1 |
| 8,742,296 B2 * | 6/2014 | Bermudez | 43/132.1 |
| 8,747,739 B2 * | 6/2014 | Parker et al. | 422/33 |
| 8,808,721 B2 * | 8/2014 | Banfield et al. | 43/123 |
| 8,931,206 B2 * | 1/2015 | Olson et al. | 43/125 |
| 8,959,831 B2 * | 2/2015 | Smith | 43/123 |
| 2002/0182104 A1 * | 12/2002 | Carman et al. | 422/28 |
| 2006/0144811 A1 * | 7/2006 | Cheng | 215/222 |
| 2007/0193454 A1 * | 8/2007 | Brown | 422/32 |
| 2009/0068071 A1 | 3/2009 | Hamilton | |
| 2009/0145020 A1 * | 6/2009 | McKnight | 43/123 |
| 2009/0200198 A1 * | 8/2009 | Guelzow et al. | 422/4 |
| 2009/0223115 A1 * | 9/2009 | Lang et al. | 43/123 |
| 2011/0113674 A1 * | 5/2011 | Levy | 43/132.1 |
| 2011/0138678 A1 * | 6/2011 | Smith | 43/107 |
| 2011/0213038 A1 * | 9/2011 | Bedoukian | 514/678 |
| 2011/0289825 A1 * | 12/2011 | James | 43/132.1 |
| 2011/0308139 A1 * | 12/2011 | James | 43/132.1 |
| 2011/0318232 A1 * | 12/2011 | Patcheak et al. | 422/129 |
| 2012/0060407 A1 * | 3/2012 | Lindsey | 43/124 |
| 2012/0186138 A1 * | 7/2012 | Bell et al. | 43/125 |
| 2012/0186140 A1 * | 7/2012 | Raud et al. | 43/132.1 |
| 2012/0192479 A1 * | 8/2012 | Schmitz | 43/132.1 |
| 2012/0216444 A1 * | 8/2012 | Raud et al. | 43/132.1 |
| 2012/0233907 A1 * | 9/2012 | Pattison et al. | 43/124 |
| 2012/0240451 A1 * | 9/2012 | Ricks | 43/132.1 |
| 2012/0311920 A1 * | 12/2012 | Olson et al. | 43/132.1 |
| 2012/0317870 A1 * | 12/2012 | Pratt | 43/132.1 |
| 2013/0125449 A1 * | 5/2013 | Winston | 43/125 |
| 2013/0180162 A1 * | 7/2013 | Vasudeva et al. | 43/123 |
| 2013/0263496 A1 * | 10/2013 | Maloney et al. | 43/132.1 |
| 2013/0269239 A1 * | 10/2013 | Whitley et al. | 43/132.1 |
| 2013/0276358 A1 * | 10/2013 | Knote et al. | 43/132.1 |
| 2014/0013653 A1 * | 1/2014 | Lander | 43/132.1 |
| 2014/0026469 A1 * | 1/2014 | Balcarek et al. | 43/132.1 |
| 2014/0041284 A1 * | 2/2014 | Nugent | 43/132.1 |
| 2014/0173970 A1 * | 6/2014 | Martin | 43/124 |
| 2014/0290124 A1 * | 10/2014 | Aidan | 43/132.1 |
| 2015/0052800 A1 * | 2/2015 | Timbrook et al. | 43/132.1 |

FOREIGN PATENT DOCUMENTS

| | | | | |
|---|---|---|---|---|
| DE | 19507477 A1 * | 9/1996 | | A01M 13/00 |
| DE | 19513909 C1 * | 9/1996 | | A01M 13/00 |
| DE | 10253563 A1 | 5/2004 | | |
| DE | 10300169 A1 * | 7/2004 | | A01M 1/20 |
| JP | 54005038 A * | 1/1979 | | A01M 13/00 |
| JP | 62033102 A * | 2/1987 | | A01M 13/00 |
| JP | 02039840 A * | 2/1990 | | A01M 1/00 |
| JP | 02069128 A * | 3/1990 | | A01M 1/00 |
| JP | 02144066 A * | 6/1990 | | A01M 1/00 |
| JP | 02156984 A * | 6/1990 | | A01M 13/00 |
| JP | 02234626 A * | 9/1990 | | A01M 1/00 |
| JP | 05115236 A * | 5/1993 | | A01M 1/00 |
| JP | 5146240 A | 6/1993 | | |
| JP | 05146240 A * | 6/1993 | | A01M 1/00 |
| JP | 05176663 A * | 7/1993 | | A01M 1/20 |
| JP | 05219871 A * | 8/1993 | | A01M 1/00 |
| JP | 07008148 A * | 1/1995 | | A01M 13/00 |
| JP | 07031349 A * | 2/1995 | | A01M 1/20 |
| JP | 07050970 A * | 2/1995 | | A01M 1/00 |
| JP | 07155099 A * | 6/1995 | | A01M 13/00 |
| JP | 07250602 A * | 10/1995 | | A01M 1/00 |
| JP | 2000116301 A * | 4/2000 | | A01M 1/00 |
| JP | 2000166451 A * | 6/2000 | | A01M 1/00 |
| JP | 2001045870 A * | 2/2001 | | A01M 1/00 |
| JP | 2001120145 A * | 5/2001 | | A01M 1/00 |
| JP | 2002272341 A * | 9/2002 | | A01M 1/00 |
| JP | 2004208534 A * | 7/2004 | | A01M 13/00 |
| JP | 2012065677 A * | 4/2012 | | A01M 1/00 |
| JP | 2012240929 A * | 12/2012 | | A01M 1/20 |
| JP | 2013039571 A * | 2/2013 | | A01M 17/00 |
| WO | WO 2005039654 A1 * | 5/2005 | | A01M 17/00 |
| WO | WO 2005046743 A1 * | 5/2005 | | A01M 1/20 |
| WO | WO 2007147569 A1 * | 12/2007 | | A01M 13/00 |

OTHER PUBLICATIONS

English abstract for JP-5146240.
English abstract for DE10253563.

* cited by examiner

METHOD AND A KIT OF PARTS FOR DECONTAMINATING A MATTRESS OR OTHER EFFECTS

This application claims priority to PCT/GB2010/050644, filed on Apr. 20, 2010, which claims priority to GB 0906754.7, filed on Apr. 20, 2009, both of which are hereby incorporated by references in their entirety.

TECHNICAL FIELD

The present invention relates to a method and kit of parts for decontaminating a mattress or other effects, and more particularly to an effective method of treating bedbug infested mattresses or other effects. These include clothing, soft furnishings, such as curtains and bedding, luggage and valuable electronic devices such as televisions, phones and computers.

BACKGROUND OF THE INVENTION

There are two main species of bedbugs:
Cimex lectularius (common bed bug); and
Cimex hemipterus (tropical bed bug).
Bed bugs are parasites that preferentially feed on humans. They are a persistent pest and have developed a number of highly evolved abilities to remain close to humans.

Bed bugs were common in the UK prior to World War II, after which time widespread use of synthetic insecticides such as DDT greatly reduced their numbers. At one stage in the 1930's 25% of all homes in the UK were infested.

In the past decade, bed bugs have begun making a comeback across the world. Although they are not considered to be a major pest or health hazard they can be highly unpleasant to live with and can cause a severe lack of sleep. International travel and commerce are thought to facilitate the spread because eggs, young, and adult bed bugs are readily transported in luggage, clothing, bedding, and furniture. Bed bugs can infest aircraft, ships, trains, and buses. Bed bugs are most frequently found in dwellings with a high rate of occupant turnover, such as hotels, motels, hostels, dormitories, shelters, apartment complexes, tenements, and prisons. Adult bed bugs are brown to reddish-brown, oval-shaped, flattened, and about 0.4 cm to 0.45 cm long. Their flat shape enables them to readily hide in cracks and crevices.

Female bed bugs lay from one to twelve eggs per day, which are deposited on rough surfaces or in cracks and crevices. The eggs are coated with a sticky substance so they adhere to the substrate. Eggs hatch in around 10 days, and nymphs can immediately begin to feed. They require a blood meal in order to moult and develop into the next stage. Bed bugs reach maturity after five moults. Developmental time (egg to adult) is affected by temperature and takes about 21 days at 30° C. to 120 days at 18° C. The nymphal period is greatly prolonged when food is scarce. The adults' lifespan may be as much as 12-18 months and they are known to be able to survive for 12 months between feeds.

Bed bugs are fast moving insects that are nocturnal blood-feeders using a barbed spike to penetrate the skin by repeatedly hammering at the surface. Nymphs may become engorged with blood within three minutes, whereas a full-grown bed bug usually feeds for ten to fifteen minutes. They then crawl away to a hiding place to digest the meal. A full meal may take 3 or 4 days to digest.

Bed bugs hide during the day in dark protected sites; they prefer fabric, wood, and paper surfaces. They usually occur in fairly close proximity to the host, although they can travel relatively large distances. Bed bugs initially can be found in seams, and folds of mattresses, later spreading to crevices in the bedstead.

When infestations are found, hotel rooms in particular may undergo chemical treatments, but not all treatments are effective at killing all forms of the insect, namely: eggs, larvae and adults. As a consequence many of the upmarket hotels take the view that the mattress and soft furnishings should be destroyed. As the mattress is often the most expensive item this is a costly and wasteful exercise.

It is an object of the present invention to provide a relatively cheap and effective method for treating mattresses or other effects to decontaminate them after they have been the subject of an insect infestation, particularly one involving bed bugs.

US 2009/0068071 discloses an apparatus and method for sterilizing, disinfecting, and preserving objects by utilizing both electromagnetic radiation to kill anaerobic pathogens and oxygen depletion to kill aerobic pathogens. The device used comprises a canister constructed in order to achieve and maintain a vacuum into which the target object is placed. Airtight valves in the apparatus allow air to be evacuated and nitrogen to be pumped in.

The applicant is however unaware of any research into the killing of bed bugs using oxygen depletion.

PRESENT INVENTION

According to a first aspect of the present invention there is provided a method for decontaminating a mattress or other effect of bed bugs comprising the steps of:
Placing the mattress or other effect in a hermetically sealable container of a size and shape commensurate with that of the mattress or other effect;
Inserting an appropriate quantity of an oxygen scavenger into the container;
Hermetically sealing the container so as to prevent ingress of oxygen; and
Leaving it for a time sufficient for the oxygen levels to be depleted to less than 0.2% and the bed bugs and their eggs and larvae to be destroyed.

Preferably the oxygen scavenger is provided in a pack comprising a permeable or semi permeable membrane (thereby containing it) which is wrapped in an air tight protective packaging. It can be activated by removing the air tight protective packaging whereupon it can be placed in the container along with the mattress and the container sealed.

In one embodiment the oxygen scavenger is a ferrous scavenger although the skilled person will readily recognise that other oxygen scavengers may be used.

An exemplary scavenger (and pack) is one provided by SJC Corp, Korea as described in Example 1.

This sachet formulation of the pack of Example 1 was however specifically developed by the manufacturer as a hand warmer and is provided in a pack size of 34 g.

The pack contains a mixture of iron dust, activated charcoal powder, cellulose, zeolite, sodium chloride and moisture (bound). This is packaged in a semi-permeable 80 mm×50 mm×10 mm sachet. The sachet is packed in a slightly larger outer sachet which is fabricated from a hermetically sealed oxygen barrier film. The pad automatically activates once the outer sachet is opened as atmospheric oxygen enters the sachet through the semi permeable membrane and reacts with the virgin iron dust which has been excluded from contact with air since its manufacture.

The oxygen oxidises the iron and the process is exothermic thereby generating heat. The sodium chloride acts as a catalyst. Once the reaction starts, heat is generated and the reaction continues until all the iron is converted. Under normal circumstances, the reaction of the unpackaged formulation is quite fast and high temperatures can be achieved in a short time. However the inclusion of other materials such as charcoal and zeolite controls and slows the rate of reaction.

Packaging the mixture in a semi-permeable sachet further controls the reaction rate, by slowing the ingress of oxygen.

The reaction is:

$$4Fe+3O_2 \rightarrow 2Fe_2O_3.$$

In separate reactions, some water is also released, due to bound water evaporating from some of the other components present which include cellulose, zeolite and sodium chloride. The heat and moisture generated additionally serve to draw the bed buds from their hiding places in the mattress or the other effect. The amount of scavenger required will depend on the effect being treated. For many applications larger pack sizes are required and, for a King Size mattress (and depending on the scavenger used) as much as 3 Kg of scavenger material may be required.

It may be appropriate to provide a plurality of smaller packs, which can be positioned in different parts of the container, e.g. for a King size mattress three 500 g packs may be positioned along the length of the mattress (top, middle, and bottom) on both sides.

The container (usually a flexible bag) may be adapted, by for example, the inclusion of pouches, to facilitate the positioning of packs evenly throughout the container.

In a preferred embodiment the container is produced "in situ" from, for example a flexible material such as laminated sheet or film. A preferred material is a laminated aluminum film or bag which can be heat and hermetically sealed around its edges. The scavenger packs can, for example, be positioned, or stuck with tape onto the sheet and the mattress or other effect to be treated positioned over it, and the sheet folded over the mattress or other effect before its two edges and top are sealed.

According to a second aspect of the present invention there is a kit of parts for use in decontaminating a mattress or other effect comprising:
 a sealable container, or a sheet like material for forming a container, of a size and shape commensurate with that of the mattress or other effect; and
 one or a plurality of oxygen scavenger packs.

The kit may additionally comprise one or more of an instruction sheet, a heat sealer, an oxygen monitor and labels. A transit bag may also be provided. The various aspects of the invention will be described further, by way of example, with reference to the following figures in which.

DETAILED DESCRIPTION

Figure 1:
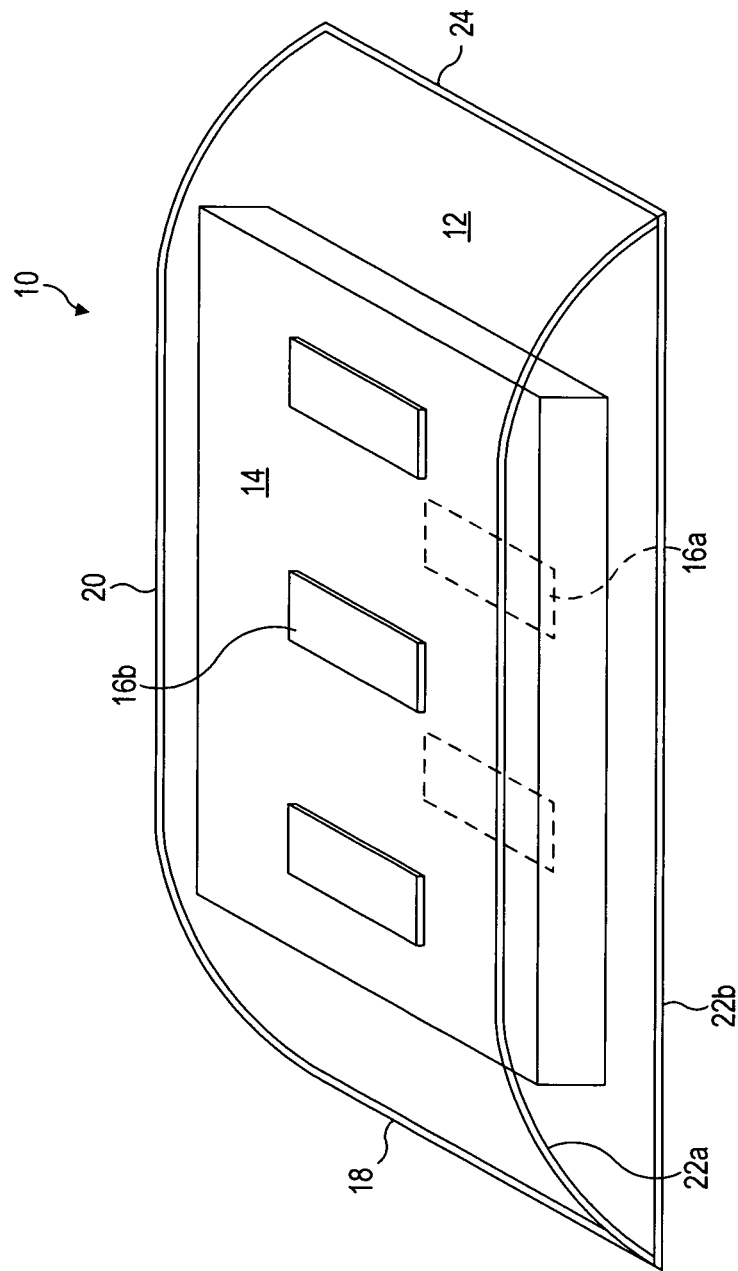
FIG. 1 is a diagrammatic representation of a mattress sealed in a container with a plurality of oxygen scavenger packs.

Referring to FIG. 1, there is illustrated a container (10) of the type used in the method of the invention. The container is made of a flexible laminated aluminium sheet (12) or any other suitable oxygen impermeable material and can be manufacture "in situ" so as to snugly surround a mattress (14) or other effect (hereafter mattress) which is to be decontaminated. By forming the container snugly around the mattress the amount of oxygen present in the container is minimised. The use of a flexible material is also beneficial in this regard. Additionally air can be drawn from the container as it is formed using e.g. a vacuum pump.

To manufacture the container in situ a suitable sized sheet is utilized. A plurality of oxygen scavenging packs (16a; 16b) may be opened, to activate them, and placed on the sheet. The mattress may then be placed on the sheet over the oxygen scavenging packs (16a) and further oxygen scavenging packs (16b) placed on the top of the mattress. The sheet is then folded over the mattress along bottom edge (18) and the container is then hermetically sealed using a heat sealer along edges (20), (22a, 22b) (shown unsealed) and top edge (24).

Of course it is possible to use an open bag like container such that only a top edge need be sealed.

The oxygen scavenger pack or packs (16) are much simpler to use than methods which might flush out oxygen using an inert gas such as nitrogen and avoid issues which can arise because of the restrictions of diffusion and interstitial oxygen.

For the method to work, sufficient oxygen scavenging material must be present. Using a ferrous oxygen scavenger, as described in Example 1 below, it has been found that about 3 Kg of materials are required to remove the oxygen to effective insecticidal levels (below about 0.2% oxygen). By using a plurality of packs the available surface area is increased which, together with their placement throughout the container, improves efficiency.

Example 1

Scavenger Pack—3 Kg for a King Sized Bed

| Iron powder | 50% |
|---|---|
| Activated Carbon | 25% |
| Sodium Chloride | 5% |
| Water | 20% |

The applicant has found that using scavenger packs of the material indicated, at the quantities indicated, oxygen levels are reduced to below 0.2% in around 3 days and that by keeping the mattresses sealed in the containers for a period of at least 10 days and preferably a few weeks, depending on temperature, will kill all forms of bed bugs.

The actual period will depend on temperature and thus at about 20° C. a period of about 10 days is required whereas at 15° C. a much longer period of 30 days has been found necessary. Much below this temperature the process is ineffective.

The methodology and kit described simplify use of a methodology (removal of oxygen) which has to date only been used in limited situations, such as in the food industry.

Once treated the effects can be cleaned or vacuumed to remove dead insects.

Example 2

Use of Anoxia to Control the Common Bedbug
*Cimex lectularius*

In this example the effect of anoxia on bed bugs was determined.
1. Objective
 The laboratory trial was carried out to determine the effect of Anoxia on common bedbug—*Cimex lectularius*.

2. Methodology Adopted

A king sized FlexiBag (8×8 ft) was placed in an area which was free from sharp projections. A large mattress (Sleepwell® 6½×3½×½ ft) made out of coir and sponge had four slits made into the fabric, at four locations (corners). Four Cardboard boxes (12×12×12 cm) were infested with bedbugs @ 40 bugs per box including eggs, different instars of nymphs and adults. Then, these infested boxes were introduced deep inside the mattress at each of the four openings. Three packs of activators were placed on the mattress, each 1 meter apart. The mattress and activator was introduced into the FlexiBag. The probe of an Oxygen meter and a Tinytag meter were placed on top of the mattress. Finally, the bag was sealed carefully with the hand held sealer.

The time, ambient temperature, and relative humidity were recorded. The oxygen readings were recorded every 4 hours during day time (only between 9.00 to 17.00 hrs) on a daily basis.

After 10 days, the FlexiBag was opened and the mattress was removed. The bedbugs were extracted and the survival recorded.

Results

Table 1 shows the total mortality of bedbugs including eggs, different nymphal instars and adults in all the four cardboard boxes, after a 10 day exposure period.

TABLE I

Effect of Anoxia on Common bedbug, *Cimex lectualrius*, under laboratory conditions

| Cardboard boxes | Number & stages of bedbugs released | | | | | Number & stages of bedbugs dead | | | | |
|---|---|---|---|---|---|---|---|---|---|---|
| | | Nymphs | Adults | | | | Nymphs | Adults | | |
| | Eggs | (different stages) | Male | Female | Total | Eggs | (different stages) | Male | Female | Total |
| Box 1 | 5 | 25 | 5 | 5 | 40 | # 0 | 25 | 5 | 5 | 40 |
| Box 2 | 5 | 25 | 5 | 5 | 40 | # 0 | 25 | 5 | 5 | 40 |
| Box 3 | 5 | 25 | 5 | 5 | 40 | 3 | 25 | 5 | 5 | 40 |
| Box 4 | 5 | 25 | 5 | 5 | 40 | 4 | 25 | 5 | 5 | 40 |
| * Box 5 Control | 5 | 25 | 5 | 5 | 40 | 0 | 5 (4 of them were first | 0 | 0 | 5 |

* Control box kept in the same lab where trial was conducted
All the eggs were hatched, but, none of the hatched ones survived
Note:
All the eggs in the control were hatched and young ones are normal Table 2 shows oxygen depletion with time.

TABLE 2

Observations on rate of Oxygen depletion across the time line

| Date | Hours/Days after activation | % Oxygen inside the bag (reading from Oxygen Analyzer) | % Oxygen depletion across the time line |
|---|---|---|---|
| 20 Jan. 2010 | Initial reading | 20.9 | — |
| | within 2 min | 17.1 | 18.18 |
| 21 Jan. 2010 | After 4 hrs | 12.7 | 39.23 |
| | After 8 hrs | 6.4 | 69.37 |
| | After 12 hrs | 3.9 | 81.33 |
| | After 16 hrs | 2.5 | 88.03 |
| | After 20 hrs | 1.7 | 91.86 |
| 22 Jan. 2010 | 2 days | 0.8 | 96.17 |
| | | 0.8 | 96.17 |
| | | 0.8 | 96.17 |
| 23 Jan. 2010 | 3 days | 0.3 | 98.56 |
| | | 0.1 | 99.52 |
| | | 0.1 | 99.52 |
| 24 Jan. 2010 | 4 days | 0.1 | 99.52 |
| | | 0.1 | 99.52 |
| | | 0.1 | 99.52 |
| 25 Jan. 2010 | 5 days | 0.1 | 99.52 |
| | | 0.1 | 99.52 |
| | | 0.1 | 99.52 |
| 26 Jan. 2010 | 6 days | 0.1 | 99.52 |
| | | 0.1 | 99.52 |
| | | 0.1 | 99.52 |
| 27 Jan. 2010 | 7 days | 0.1 | 99.52 |
| | | 0.1 | 99.52 |
| | | 0.1 | 99.52 |
| 28 Jan. 2010 | 8 days | 0.1 | 99.52 |
| | | 0.1 | 99.52 |
| | | 0.1 | 99.52 |
| 29 Jan. 2010 | 9 days | 0.1 | 99.52 |
| | | 0.1 | 99.52 |
| | | 0.1 | 99.52 |
| 30 Jan. 2010 | 10 days | 0.1 | 99.52 |
| | | 0.1 | 99.52 |
| | | 0.1 | 99.52 |

Further observations on the temperature and relative humidity generated by the oxygen scavengers, were made.

Figure 2:
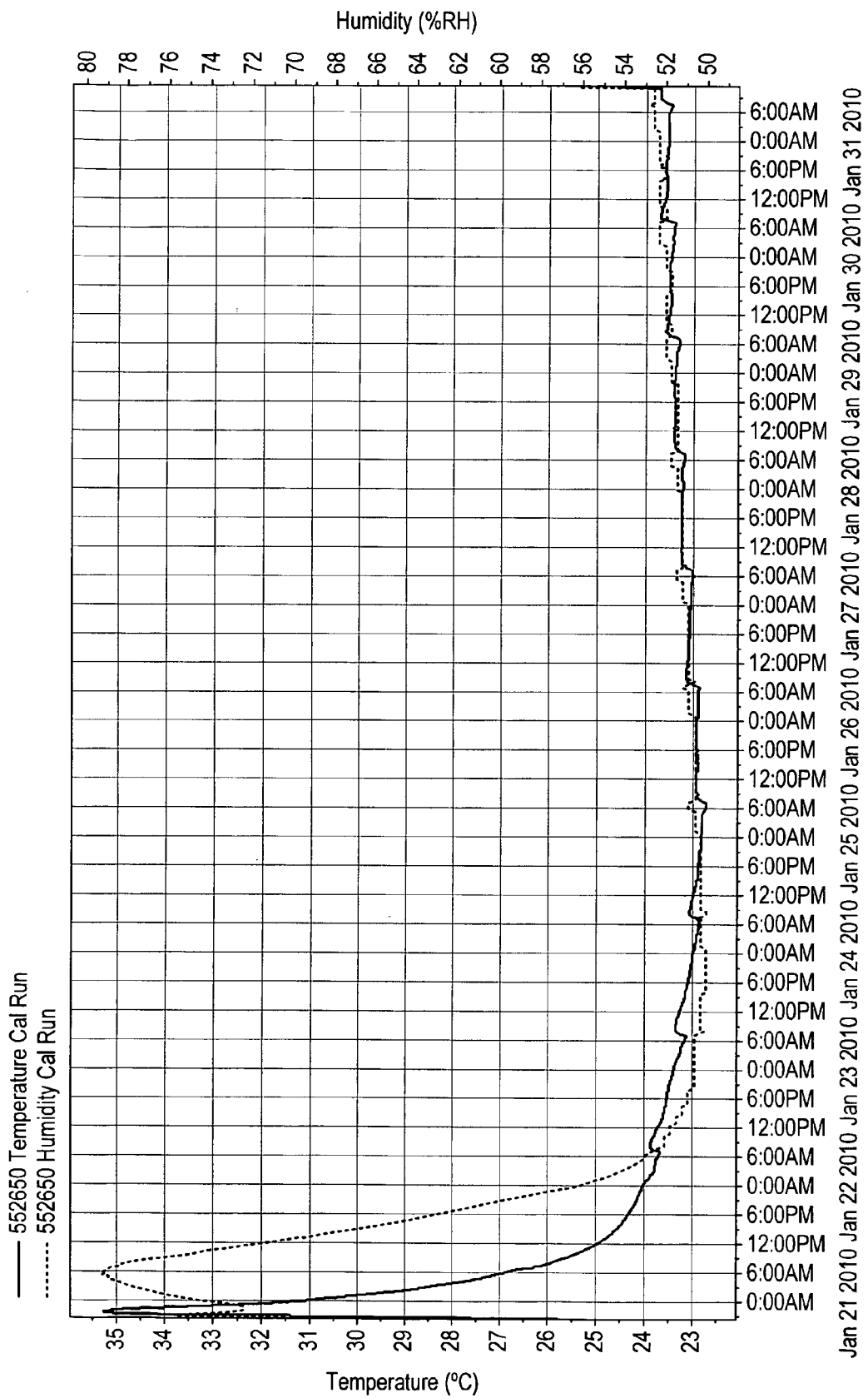
FIG. 2 is a graph showing the temperature and relative humidity profile during treatment of a mattress inside the bag.

FIG. 2 shows the temperature/relative humidity profile inside the bag. It shows the generation of heat and humidity on activation but as the oxygen is depleted these drop.

Figure 3:
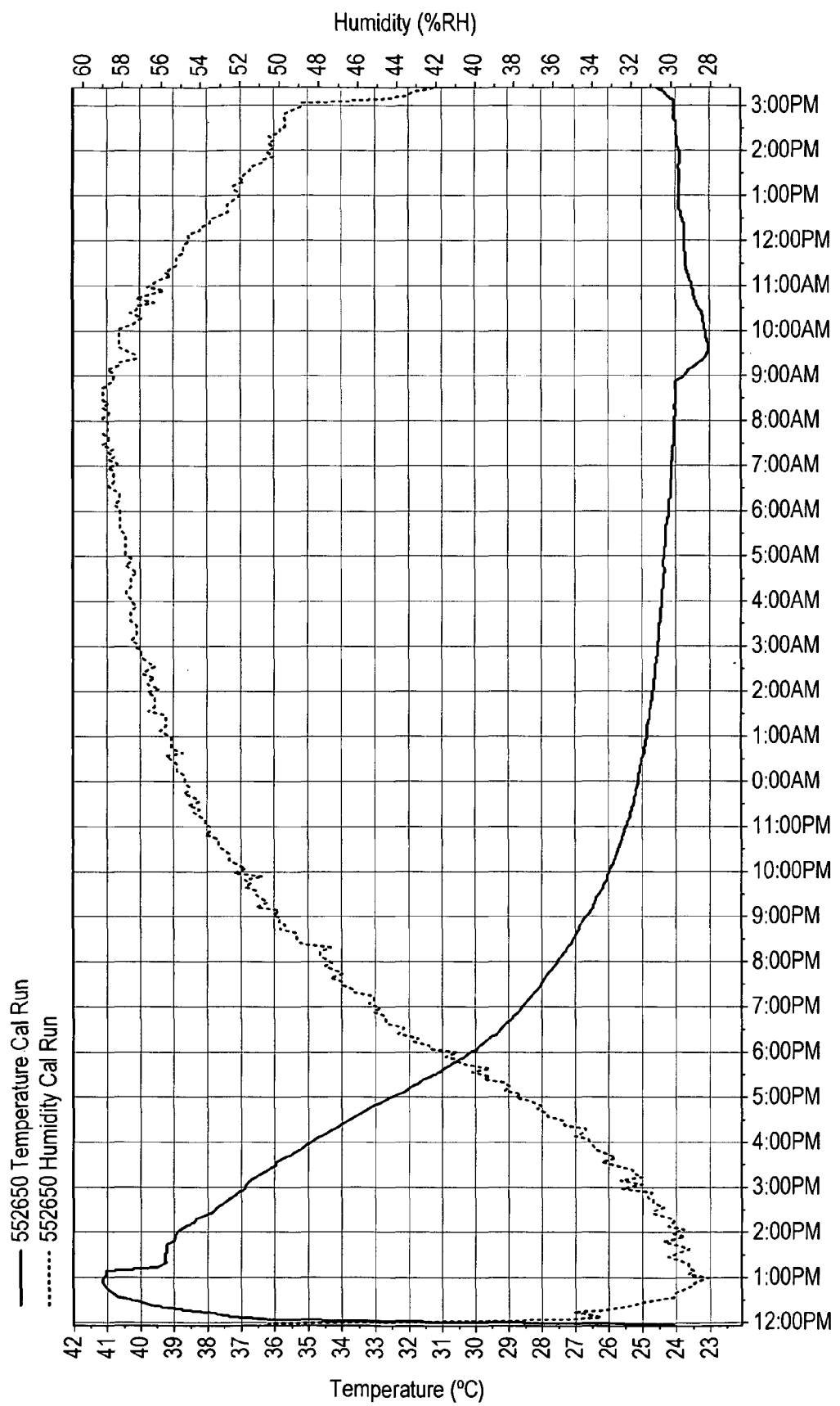
FIG. 3 is a graph showing the temperature and relative humidity profile generated from the used activators after they are taken from the bag (10 days later).

FIG. 3 shows how the temperature and relative humidity generated by the activators after they were removed from the bag. It demonstrates an "excess" of activators were used.

The invention claimed is:

1. A method for decontaminating a mattress or other effect of bed bugs comprising the steps of:
    placing the mattress or other effect, which is infested with at least one of the bed bugs, bed bug eggs, and bed bug larvae, in a hermetically sealable container of a size and shape commensurate with that of the mattress or other effect;
    inserting an appropriate quantity of an oxygen scavenger which in addition to utilising oxygen on activation, generates heat and moisture into the container;
    hermetically sealing the container so as to prevent ingress of oxygen; and
    leaving the container for a time sufficient for the oxygen levels to be depleted to less than 0.2% and the bed bugs and their eggs and larvae to be destroyed, wherein the moisture generated by the oxygen scavenger within the hermetically sealed container results in a relative humidity in the container which is sustained at least until meeting the time sufficient for the oxygen levels to be depleted to less than 0.2%.

2. A method for decontaminating a mattress as claimed in claim 1 wherein the oxygen scavenger is provided in a pack.

3. A method for decontaminating a mattress as claimed in claim 1 wherein the oxygen scavenger is provided in a plurality of packs, wherein the plurality of packs are placed in the container.

4. A method as claimed in claim 1 wherein the oxygen scavenger comprises a ferrous material.

5. A method as claimed in claim 1 wherein the container comprises a flexible material.

6. A method as claimed in claim 5 wherein the material is a laminated sheet material.

7. A method as claimed in claim 6 wherein the laminated sheet material is a laminated aluminum.

8. A method as claimed in claim 1 wherein the container is hermetically sealed using a heat sealing method.

9. A method as claimed in claim 1 wherein the oxygen scavenger comprises a ferrous material and the container comprises a flexible material.

10. A method as claimed in claim 1, wherein the oxygen scavenger generates moisture having the relative humidity of at least 50%.

11. A method as claimed in claim 10, wherein the relative humidity of at least 50% is sustained at least until meeting the time sufficient for the oxygen levels to be depleted to less than 0.2%.

12. The method of claim 11, wherein the relative humidity of at least 50% is sustained until all the bed bugs and their eggs and larvae are destroyed.

13. A method as claimed in claim 1, wherein the oxygen scavenger generates heat having a temperature of at least 15° C., the temperature of at least 15° C. being maintained during the time sufficient for the oxygen level to be depleted to less than 0.2% and the bed bugs and their eggs and larvae to be destroyed.

14. A method for decontaminating a mattress or other effect of bed bugs comprising the steps of:
    placing the mattress or other effect, which is infested with at least one of the bed bugs, bed bug eggs, and bed bug larvae, in a hermetically sealable container of a size and shape commensurate with that of the mattress or other effect;
    inserting an appropriate quantity of an oxygen scavenger which in addition to utilising oxygen on activation, generates heat and moisture into the container;
    hermetically sealing the container so as to prevent ingress of oxygen; and
    leaving the container for a time sufficient for the oxygen levels to be depleted to less than 0.2% and the bed bugs and their eggs and larvae to be destroyed, wherein the oxygen scavenger is provided in a plurality of packs, the plurality of packs are placed in the container, wherein the oxygen scavenger comprises a ferrous material and the container comprises a flexible material, wherein the moisture generated by the oxygen scavenger within the hermetically sealed container results in a relative humidity in the container which is sustained at least until meeting the time sufficient for the oxygen levels to be depleted to less than 0.2%.

15. A method as claimed in claim 14, wherein the oxygen scavenger generates moisture having the relative humidity of at least 50%.

16. A method as claimed in claim 15, wherein the relative humidity of at least 50% is sustained at least until meeting the time sufficient for the oxygen levels to be depleted to less than 0.2%.

17. A method as claimed in claim 14, wherein the oxygen scavenger further includes a bound moisture source.

18. A method for decontaminating a mattress or other effect of at least one bed bug comprising the steps of:
    placing the mattress or other effect, which is infested with the at least one bed bug, in a hermetically sealable container of a size and a shape commensurate with that of the mattress or other effect;
    inserting an appropriate quantity of an oxygen scavenger into the container, wherein the oxygen scavenger which in addition to utilizing oxygen on activation, generates heat and moisture having a relative humidity of at least 50%;
    hermetically sealing the container so as to prevent an ingress of oxygen; and
    leaving the container for a time sufficient for an oxygen level to be depleted to less than 0.2% and the at least one bed bug to be destroyed;
    wherein the moisture generated by the oxygen scavenger within the hermetically sealed container results in the relative humidity of at least 50% being maintained during the time sufficient for the oxygen level to be depleted to less than 0.2%.

\* \* \* \* \*